United States Patent [19]

Semersky

[11] 4,235,725
[45] Nov. 25, 1980

[54] STERILE BLOOD-COLLECTING AND SEPARATING DEVICE

[75] Inventor: Frank E. Semersky, Toledo, Ohio

[73] Assignee: Owens-Illinois, Inc., Toledo, Ohio

[21] Appl. No.: 934,240

[22] Filed: Aug. 16, 1978

[51] Int. Cl.³ .............................................. B01D 21/26
[52] U.S. Cl. ............................ 210/516; 210/DIG. 24; 210/927; 422/22; 53/405; 53/425
[58] Field of Search ................. 210/83, 516, DIG. 23, 210/DIG. 24

[56] References Cited

U.S. PATENT DOCUMENTS

| | | | |
|---|---|---|---|
| 3,579,303 | 5/1971 | Pickering | 23/230 |
| 3,743,480 | 7/1973 | Falk | 195/1.8 X |
| 3,780,935 | 12/1973 | Lukacs | 210/83 X |
| 3,852,194 | 12/1974 | Zine, Jr. | 210/DIG. 23 |
| 3,854,875 | 12/1974 | Bosshardt | 210/64 X |
| 3,977,982 | 8/1976 | Hertl | 210/DIG. 23 |
| 3,997,442 | 12/1976 | Gigliello et al. | 210/83 |
| 4,021,340 | 5/1977 | Zine, Jr. | 210/DIG. 23 |
| 4,043,928 | 8/1977 | Lukacs et al. | 252/60 |
| 4,049,692 | 9/1977 | Zine, Jr. | 210/83 X |
| 4,055,501 | 10/1977 | Cornell | 210/516 |
| 4,071,316 | 1/1978 | Wright | 210/DIG. 23 |
| 4,083,784 | 1/1978 | Zine, Jr. | 210/DIG. 23 |
| 4,088,582 | 5/1978 | Murty et al. | 210/DIG. 23 |

*Primary Examiner*—John Adee
*Attorney, Agent, or Firm*—John R. Nelson; Myron E. Click; David H. Wilson

[57] ABSTRACT

A pre-packaged blood collecting and separating device and process of its preparation are disclosed in which the device contains a mixture of liquid polybutadiene and an inorganic, inert filler, such as silica, as a thixotropic gel adapted at rest to form a sealing barrier between separated blood phases. The device and gel are subjected to sterilizing radiation to form a substantially sterile device, substantially free of backflow contamination, without degradation of the physical properties of the gel.

16 Claims, 4 Drawing Figures

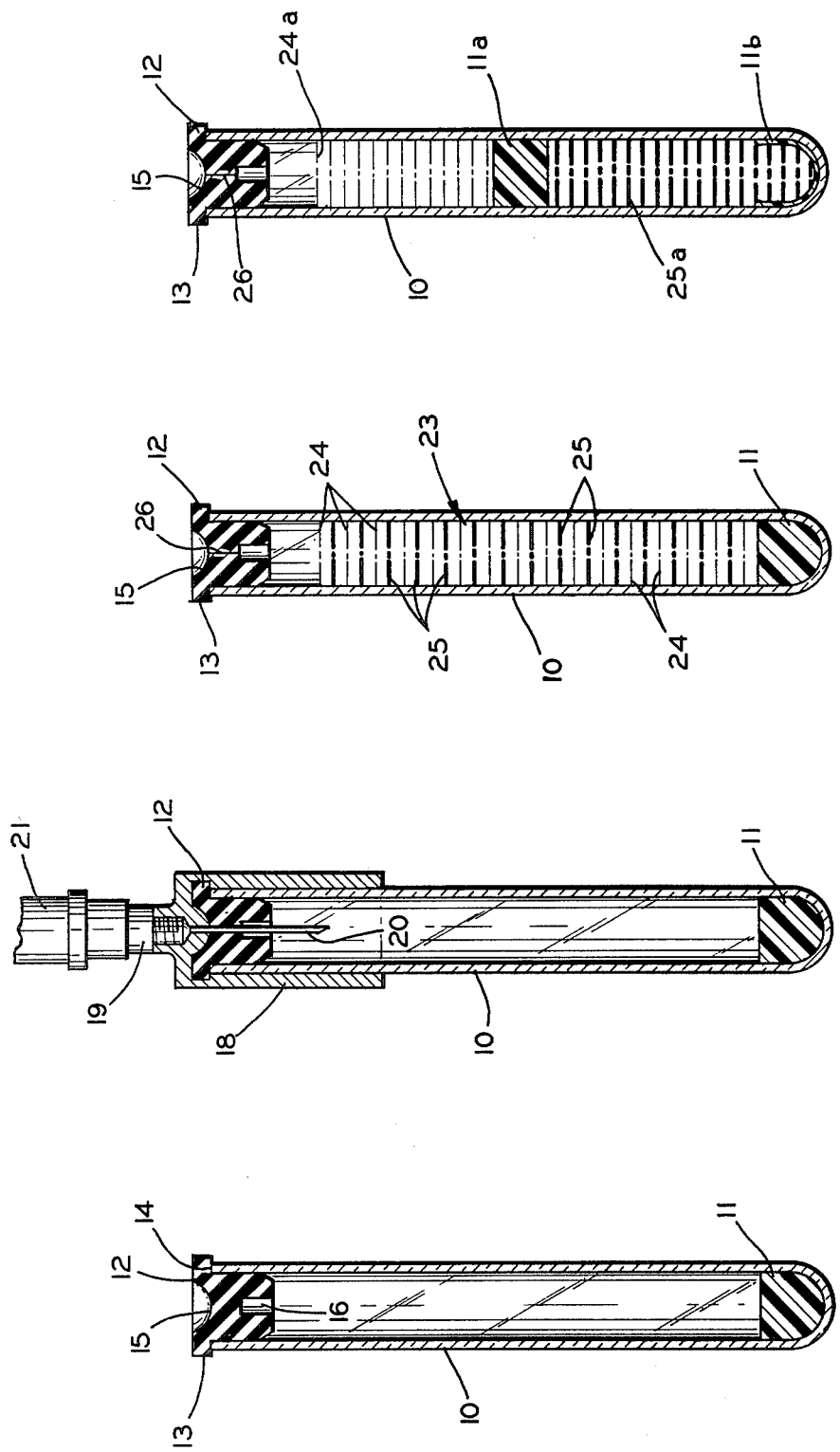

4,235,725

STERILE BLOOD-COLLECTING AND SEPARATING DEVICE

BACKGROUND OF THE INVENTION

The present device may be used in separating any fluid having at least two phases of differing densities, such as plasma, cellular material, or platelets. However, the following description is directed to the collection and separation of whole human blood for which the device is especially adapted.

It is an established practice to centrifuge blood to effect a separation into its two major components or phases, namely, a light serum portion and a heavier clot portion consisting mainly of red blood cells. Such separation of whole blood into its two principal phases has greatly facilitated physical and chemical analyses of blood.

However, simple centrifugation of whole blood does not necessarily effect an ideal separation for analytical purposes. It is known, for example, that once blood phases are separated, if the lighter phase is not removed within a relatively short time, interaction occurs between the separated phases and inaccurate test results are apt to be obtained. Moreover, clinics and hospitals are meeting increasing demands on their services for more routine as well as specialized diagnostic tests of blood.

In an attempt to overcome the problems associated with simple centrifugation, it has been proposed to use various materials or compositions having a specific gravity between those of the serum and clot portions to assist in separating such portions. These compositions have physical and chemical properties which, in the presence of whole blood, permit the composition to be centrifuged to a position intermediate that of the serum and clot portions and thereby form a sealing barrier or partition between the two portions. For the composition to function as a barrier, it must be viscous at rest, like petroleum jelly, and yet flow freely under centrifugal forces to a proper position between the two blood phases.

For example, the earliest attempt known to applicant to provide a sealant material comprises a mixture of a silicone fluid, particularly polysiloxanes, and silica as illustrated by U.S. Pat. No. 3,780,935 to Lukacs et al, U.S. Pat. No. 3,852,194 to Zine, and U.S. Pat. No. 4,043,928 to Lukacs et al. U.S. Pat. No. 3,977,982 to Hertl, U.S. Pat. No. 4,083,748 to Zine, and U.S. Pat. No. 4,043,784 to Zine also describe compositions for this purpose comprising a silicone fluid and silica in which the silicone fluid may be polysiloxanepolyoxyalkyl copolymers.

U.S. Pat. No. 4,021,340 to Zine suggests using, in lieu of a silicone fluid-silica system, one comprising a liquid polybutene having dispersed therein a siliceous filler. U.S. Pat. No. 4,055,501 to Cornell describes a three component system for a barrier for separating blood phases comprising a hydrocarbon polymer, a hydrophobic silica powder, and a hydrophilic silica powder. The hydrocarbon polymer may be liquid polybutene, liquid butyl rubber, or liquid polybutadiene.

While the use of thixotropic sealing barriers between separated serum and clot phases has improved the technique of sampling and analyzing whole blood, this use has not removed the danger of infecting a patient due to backflow attending the sampling of his blood. For example, in the usual sampling procedure, the practice is to withdraw blood from a vein of a patient through a tubular needle and into a specimen tube or other collection device which may be partially evacuated to assist in the blood flow. Unfortunately, the collection device often is not sterile. The backflow of blood to a patient from a collection or specimen tube, as when disconnecting the sampling apparatus, can contaminate the patient due to the carry-back of bacteria originally present within the collecting device. For example, the spread of hepatitus can occur in this manner.

Sterilization as by gamma radiation of commercial gel-containing blood collecting devices has not previously been thought to be possible, because the gels were not expected to withstand the radiation. Properties of the gels are normally altered by radiation, such that the gel can no longer function as desired. For example, commercially available silicone-based serum separator gels, particularly the polysiloxanes, set up under sterilizing radiation. Their viscosities increase greatly and they become non-flowable and rubbery.

SUMMARY OF THE INVENTION

The principal object of the present invention is to provide an improved gel-like composition which can be used as a sealant or barrier between blood phases separated as by centrifugation. A related object is to provide such a gel-like composition which can be safely subjected to sterilizing radiation without degradation or otherwise destroying its properties which enable it to be used as a sealant. The gel or gel-like composition may be radiated alone by itself or preferably while it occupies an enclosure such as an enclosed blood collecting and separating device. In the latter instance, a pre-packaged, substantially sterile blood collecting and separating device can be manufactured which is substantially free of backflow contamination of a patient. The prepackaged device is ready for use without any further preparation.

In one form, the present gel-like composition that is adapted for use as a sealing barrier between separated phases of differing densities of a fluid, especially whole blood, has at rest a density intermediate the differing densities and comprises liquid polybutadiene and an inorganic, inert filler dispersed therein. The filler is preferably silica and present in an amount to impart a desired density to the gel-like composition. Normally, the gel-like composition comprises about 100 parts by weight of liquid polybutadiene and from about 20 parts to about 60 parts of the inorganic filler.

In the preferred practice, the gel-like composition is placed in a blood collecting and separating device which is then partially evacuated and stoppered. The enclosed device and gellike composition are then subjected to sterilizing radiation, such as by gamma rays, without degradation of physical properties of the gel composition.

BRIEF DESCRIPTION OF THE DRAWINGS

In the accompanying drawings:

FIG. 1 is a central longitudinal section of a blood collecting and separating device having a charge of the present composition at its closed end and a penetrable plug or stopper at its normal open end;

FIG. 2 is a central longitudinal section like FIG. 1 of a blood collecting and separating device having a conventional holder and needle embracing and penetrating the plug to deliver to the device a sample of blood;

FIG. 3 is a central longitudinal section of a device like that of FIG. 2 after the blood sample has been delivered and the holder and needle removed; and FIG. 4 is a central longitudinal section of a device like that of FIG. 3 after the device has been centrifuged and the blood phases separated by a barrier or sealant formed by the gel-like composition.

DESCRIPTION OF THE PREFERRED EMBODIMENTS

The present thixotropic gel-like composition is adapted for use as a sealing barrier between separated phases of different densities of a fluid, especially whole blood. The composition has at rest a density intermediate the differing densities and comprises liquid polybutadiene and an inorganic inert filler dispersed therein. Surprisingly, this gel-like composition can safely withstand sterilizing radiation without degradation of the functional properties which enable it to perform as desired for the purpose indicated.

The polymeric growth of the polybutadiene is not critical as long as it is liquid at room temperatures. The polybutadiene may have an average molecular weight ranging from about 2600 to about 3600, although these values are not critical.

Preferably, the polybutadiene is hydroxyl-terminated, and optionally may be copolymerized with up to 25% by weight of styrene. As a single example, the polybutadiene and the styrene-butadiene copolymer can be illustrated as:

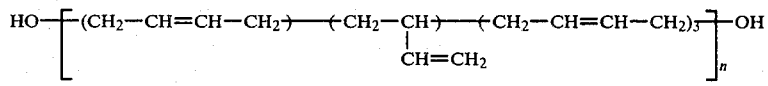

in which n may be, for example, 50; and

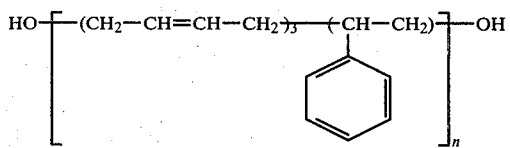

in which n may be, for example, 54.

The hydroxyl number (milligrams of KOH per gram of sample) may range from about 40 to 48 for the homopolymer and, in one instance, was 36.5 for the butadiene-styrene copolymer, although these values are not critical.

The added inorganic inert filler controls specific gravity, viscosity, and thixotropy. The filler is used in particulate form having a high surface area, for example, from about 50 to about 120 square meters per gram. The inert filler can be bentonite, talc, or alumina, but it is preferably silica and especially hydrophobic fumed silica. The hydrophobic character avoids adsorption of water-soluble components of blood.

The normal specific gravity of whole blood as determined by the pycnometric method is considered to be in the range of about 1.048 to about 1.066. After centrifuging, the specific gravity of the serum portion is about 1.026 to about 1.031, and the specific gravity of the heavier clot portion is about 1.090 to about 1.095. Accordingly, the density of the gel at rest should be intermediate these ranges or about 1.033 to about 1.088 and preferably from about 1.037 to about 1.050. As indicated, the inorganic inert filler is added in an amount to achieve a density within this latter range. Proportions are not otherwise critical. As a general rule, the present gel comprises about 100 parts by weight of liquid polybutadiene and from about 20 parts to about 60 parts by weight of the inorganic inert filler. The density desired in the gel when fluid, its rheology and thixotropic properties, and the type of inert filler chosen all play a role in determining the amount of filler used with the liquid polybutadiene. Such an amount may be easily determined by simple trial and error. For example, when fumed silica is the inert filler, excellent results are obtained when about 30 to about 40 parts of the fumed silica are used per 100 parts of liquid polybutadiene. The gel is also water insoluble and substantially non-toxic.

When silica is the inert filler, it may itself have a specific gravity of about 1.05 to about 2.65 and an average particle size of about 16 to about 20 millimicrons.

The gel composition is prepared by suitably admixing the particulate inorganic filler in the liquid butadiene, preferably while at slightly elevated temperatures and under a partial vacuum to discourage substantial further polymerization of the polybutadiene. For example, the filler and liquid butadiene can be mixed by stirring in a container while maintaining the temperature at about 60° C. and drawing a vacuum of about 0.2 atmosphere on the container. The resulting mass is a white gel.

The gel so prepared can be subjected to sterilizing radiation and then marketed in this form, preferably within an enclosed container which also safely withstands sterilizing radiation. In this case, the gel can be directly sterilized within the enclosed container. In the preferred practice, the container is the blood collecting and separating device, so the gel and the device together form a pre-packaged device which can be used at the time of taking a blood sample without any further preparation The preferred embodiment of a pre-packaged container which defines as well the blood collecting and separating device is more particularly described with reference to the accompanying figures. In FIG. 1, a blood sampling tube 10 contains a charge of the present gel composition 11 at its closed end and has a tightly fitting stopper or plug 12 at its normally open end. Gel 11 is used in an amount sufficient to form at rest a separating barrier extending across tube 10. For most sampling tubes in use, an amount of about one gram to about four grams of gel 11 suffices. Although gel 11 is shown at the bottom of tube 10, it may be placed at any convenient location within the tube. Tube 10 is partially evacuated to about 0.1 atmosphere before stopper 12 is applied. The resulting sub-atmospheric pressure in tube 10 aids in a sampling operation and collection of blood in the tube.

To aid penetration of a needle, stopper 12 has a flange 13 which rests on lip 14 of tube 10, a concavity 15 at its exposed top and a central aperture 16 at its inserted end. Stopper 12 is piercable by a needle and is self-sealing. For this purpose, the stopper may be formed of a suitable elastomer such as butyl rubber. When assembled, as shown in FIG. 1, tube 10 and its gel charge 11 are subjected to sterilizing radiation. This may be by gamma rays or x-rays or by any other irradiation suitable to result in substantial sterility. The rate of radiation is not critical within normal limits, since exposure can be extended until the desired sterility is achieved. However, for most applications, sterilizing radiation in an amount of about 2.5 to about 3.5 megarads suffices.

It is not readily understood why liquid polybutadiene safely withstands sterilizing radiation. It is known that even after formation of the present gel and its sterilizing radiation, the polybutadiene component still contains carbon-to-carbon unsaturation. It is postulated that this may explain its unexpected, safe exposure to sterilizing radiation. It is possible that the chemical unsaturation acts as a "sink" or "well" to absorb or react with free atoms or radicals released by the radiation. If sterilizing radiation of the polybutadiene were extended long enough, it is possible that it, too, would set up and be destroyed for the purpose intended. But it withstands sterilizing radiation long enough to reach a sterile state without losing its desirable functional properties. On the other hand, while radiation to the sterile state is of course desired, there may be instances where only a substantially sterile or nearly sterile condition is reached as, for instance, through insufficient exposure to radiation. Yet the resulting irradiated product does have utility and does represent a significant and unobvious improvement over prior art practice where there is essentially no sterility at all. As used here and in the claims, the term "substantially sterile" means a sterile condition or one nearly so for the reason stated.

In use, a cup-holder having a double ended hollow needle is used to obtain blood from a patient. An outer needle end (not shown) is injected into a patient's vein and then by forwardly thrusting the sampling tube on and about the holder, an inner needle punctures the stopper and blood may be collected in the tube from the patient.

FIG. 2 represents the stage of the procedure when the holder has been thrust about the sampling tube. A cup-like holder 18 with a needle mount 19 embraces the stoppered end of tube 10, while a hollow, double-ended needle 20, supported by needle cover 21, pieces stopper 12 through its concavity 15 and center aperture 16 to each the interior of tube 10.

When the desired quantity of blood has been collected, the holder 18 and attendant equipment are removed. The blood collecting and separating device then appears as shown in FIG. 3. Whole blood generally represented at 23 consists of a serum portion represented by relatively light lines 24 and a heavier clot portion represented by relatively heavy lines 25, all of which lies over gel 11. The withdrawal of needle 20 leaves a scar 26 which, because of the self-sealing nature of the rubber of stopper 12, sufficiently closes to prevent the leakage of air into tube 10.

The tube as represented in FIG. 3 is now centrifuged in a known manner, for example, for about 10 minutes at 1100 RCF. Gel 11 is thixotropic or perhaps, more accurately, pseudoplastic. At rest, the gel acts as though it is relatively thick like petroleum jelly. But under the stresses of centrifugation, it acts as though a fluid. Accordingly, during centrifugation, gel 11 in fluid state can move in either direction lengthwise of tube 10. The flow of neither the serum portion nor the clot portion is restricted or otherwise influenced by gel 11. Each of the serum and clot portions and the gel is free to seek its own path. The ultimate position of each within tube 10 is influenced solely by the effect of centrifugal force and its own specific gravity. FIG. 4 illustrates the conditions within tube 10 after centrifugation. At this time, gel 11, because of its specific gravity and other properties, has migrated to a position intermediate the serum and clot portions. Due to its thixotropic nature, the gel now at rest is once again relatively thick and prevents a serum-clot interface by forming a physical and chemical barrier indicated at 11a between the serum and clot portions indicated, respectively, at 24a and 25a. A slight coating 11b of the gel may remain at the bottom of tube 10 because of adherence to glass. Barrier 11a can withstand pressure of the heavier phase 25a when tube 10 is inverted. Accordingly, the lighter phase 24a can be removed by simply decanting from tube 10. Alternatively, pipetting can be used. Standard analytical tests are then made on the separated and colleced serum portion 24a.

WORKING EXAMPLE

An amount of 31.8 parts by weight of fumed silica sold by Philadelphia Quartz Company under the trade designation, QUSO WR-82, was added to 100 parts by weight of liquid polybutadiene, sold by the Arco Chemical Company under the trademark "poly bd." The mixture took place in a suitable container which was heated to about 60° C. and subjected to a vacuum of about 0.2 atmosphere. The resulting mass was a white gel having a specific gravity of about 1.045 with an apparent viscosity of 300,000 to 600,000 centipoises. The gel was subjected to sterilizing radiation at a maximum dosage of 2.6 megarads.

A 2.5 gram sample of the sterilized gel was then centrifuged to the bottom of an open 10 ml blood collection tube. Two 10 ml aliquots of blood were then drawn from the arm of applicant using standard venipuncture techniques. One aliquot was immediately decanted into the tube containing the present gel composition, and the other aliquot was immediately placed in another, similar tube but without any gel. Both tubes were then centrifuged at a force of 1100 times gravity for approximately 10 minutes.

The separation of the blood components in the tube containing the present gel was watched by synchronizing a strobe light on the tube during the centrifuging action. The gel moved slowly along a wall of the tube to a serum-clot interface. After centrifugation, a preliminary check of the strength of the barrier formed by the gel was determined by inverting the tube for one hour. No slumping of the gel was seen at this time.

Both tubes were then placed on ice and transported to Mercy Hospital, Toledo, Ohio for preliminary clinical evaluation of the serum components from the two tests. Table A indicates the results:

TABLE A

| TEST | TUBE 1 (With Gel) | TUBE 2 (Control-No Gel) |
|---|---|---|
| $Na^+$ (meq) | 140 | 140 |
| $K^+$ (meq) | 4.5 | 4.6 |
| $Cl^-$ (meq) | 97 | 101 |
| Glucose (mg/dl) | 76 | 77 |
| BUN (mg/dl) | 10 | 11 |
| SGOT (U) | 25 | 24 |
| LDH (U) | 131 | 129 |
| Alkaline Phosphatase (U) | 4.3 | 4.9 |
| Total Protein (g/dl) | 8.3 | 8.2 |
| $Cl^-$ (meq) | 9.3 | 9.5 |
| Cholesterol (mg/dl) | 264 | 282 |
| Bilirubin (mg/dl) | 0.5 | 0.5 |
| Creatinine (mg/dl) | 1.2 | 1.2 |

TABLE A-continued

| TEST | TUBE 1 (With Gel) | TUBE 2 (Control-No Gel) |
|---|---|---|
| Uric Acid (mg/dl) | 5.4 | 5.5 |

The results indicated that any disagreement between the two sets of test values were well within the confidence levels of the tests performed. The results can be deemed to be clinically identical. This shows that the use of the polybutadiene liquid had no known adverse effect on at least the known and common blood tests indicated.

Although the foregoing describes presently preferred embodiments of the present invention, it is understood that the invention may be practiced in still other forms within the scope of the following claims.

What I claim is:

1. In a substantially sterile, irradiated, blood collecting and separating device comprising an enclosed container adapted to receive a blood sample and having therein a thixotropic gel adapted to form a separating barrier between separated phases of said blood having differing densities, said gel having at rest a density intermediate said differing densities; the improvement wherein said gel comprises a sterilizing irradiated liquid polybutadiene still retaining carbon-to-carbon unsaturation and an inorganic inert filler dispersed therein, said gel having been subjected to sterilizing radiation without substantial loss of said carbon-to-carbon unsaturation in said butadiene, whereby said container and gel are sterilized to provide said sterile blood collecting and separating device without destruction of physical properties of said gel.

2. The blood collecting and separating device of claim 1 in which said container comprises an open-ended tube adapted for centrifuging, said open-end being closed by an elastomeric, self-sealing plug adapted to be penetrated by a needle or the like.

3. The blood collecting and separating device of claim 1 in which said filler is selected from the group consisting of silica, bentonite, alumina, and talc.

4. The blood collecting and separating device of claim 1 in which said filler is fumed silica.

5. The blood collecting and separating device of claim 1 in which said filler is present in an amount to impart a desired density to said composition.

6. The blood collecting and separating device of claim 1 in which said container is partially evacuated.

7. The blood collecting and separating device of claim 1 in which said gel comprises about 100 parts by weight of liquid polybutadiene and about 20 to about 60 parts by weight of said filler.

8. The blood collecting and separating device of claim 1 in which said gel comprises about 100 parts by weight of liquid polybutadiene and about 30 to about 40 parts of fumed silica.

9. The blood collecting and separating device of claim 1 in which said liquid butadiene is selected from the group consisting of a polymer of:

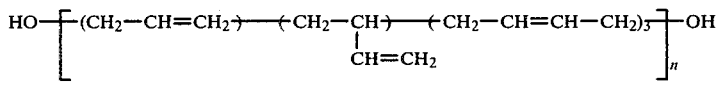

and a copolymer of said reactant with a second reactant comprising:

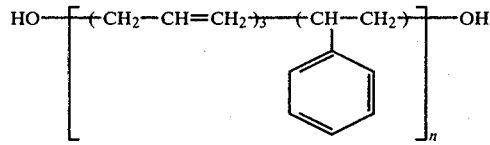

said second reactant being optionally present in an amount up to about 25% by weight of said first mentioned reactant, and the value of n in all cases being sufficiently low to impart the liquid state.

10. A process for preparing a pre-packaged, substantially sterile, blood collecting and separating device substantially free of backflow contamination, comprising:
    (a) placing within a container a quantity of a thixotropic gel sufficient to form at rest a separating barrier extending across the container, said gel comprising liquid polybutadiene and an inorganic inert filler dispersed therein,
    (b) forming a partial vacuum in said container and enclosing the partially evacuated container, and
    (c) subjecting the container and thixotropic gel to sterilizing radiation to form a substantially sterile device without degradating the physical properties of said gel.

11. The process of claim 10 in which said filler is selected from the group consisting of silica, bentonite, alumina, and talc.

12. The process of claim 10 in which said filler is fumed silica.

13. The process of claim 10 in which said filler is present in an amount to impart a desired density to said composition.

14. The process of claim 10 in which said polybutadiene of said gel still contains carbon-to-carbon unsaturation after said sterilizing radiation.

15. The process of claim 10 in which said sterilizing radiation is at an exposure of about 2.5 megarads to about 3.5 megarads.

16. The process of claim 10 in which said gel comprises about 100 parts by weight of liquid polybutadiene and about 20 to about 60 parts by weight of said filler.

* * * * *

UNITED STATES PATENT AND TRADEMARK OFFICE
CERTIFICATE OF CORRECTION

PATENT NO. : 4,235,725

DATED : November 25, 1980

INVENTOR(S) : Frank E. Semersky

It is certified that error appears in the above-identified patent and that said Letters Patent are hereby corrected as shown below:

Col. 1, line 49, "4,083,748" should be --- 4,049,692 --

Col. 6, line 16, "colleced" should be --- collected --

Signed and Sealed this

Ninth Day of June 1981

[SEAL]

Attest:

RENE D. TEGTMEYER

Attesting Officer

Acting Commissioner of Patents and Trademarks